(12) United States Patent
Liu

(10) Patent No.: US 10,485,826 B2
(45) Date of Patent: Nov. 26, 2019

(54) PHARMACEUTICAL FORMULA FOR THE TREATMENT AND/OR PREVENTION OF ARTHRITIS AND ITS MANUFACTURE

(71) Applicant: Jun Mi, Sichuan (CN)

(72) Inventor: Zijuan Liu, Rochester Hills, MI (US)

(73) Assignee: Zoesen LLC, Rochester Hills, MI (US)

( * ) Notice: Subject to any disclaimer, the term of this patent is extended or adjusted under 35 U.S.C. 154(b) by 25 days.

(21) Appl. No.: 15/544,641

(22) PCT Filed: Sep. 14, 2016

(86) PCT No.: PCT/CN2016/099076
§ 371 (c)(1),
(2) Date: Jul. 19, 2017

(87) PCT Pub. No.: WO2017/101536
PCT Pub. Date: Jun. 22, 2017

(65) Prior Publication Data
US 2018/0000860 A1    Jan. 4, 2018

(30) Foreign Application Priority Data
Dec. 14, 2015    (CN) .......................... 2015 1 0926291

(51) Int. Cl.
| | | |
|---|---|---|
| *A61K 33/04* | (2006.01) |
| *A61K 33/30* | (2006.01) |
| *A61K 9/06* | (2006.01) |
| *A61K 9/00* | (2006.01) |
| *A61K 47/10* | (2017.01) |
| *A61K 47/18* | (2017.01) |
| *A61K 47/26* | (2006.01) |
| *A61K 47/32* | (2006.01) |
| *A61K 47/06* | (2006.01) |
| *A61K 47/12* | (2006.01) |
| *A61K 47/14* | (2017.01) |
| *A61K 47/44* | (2017.01) |
| *A61K 9/70* | (2006.01) |

(52) U.S. Cl.
CPC ............ *A61K 33/04* (2013.01); *A61K 9/0014* (2013.01); *A61K 9/06* (2013.01); *A61K 9/7038* (2013.01); *A61K 9/7046* (2013.01); *A61K 9/7061* (2013.01); *A61K 9/7069* (2013.01); *A61K 33/30* (2013.01); *A61K 47/06* (2013.01); *A61K 47/10* (2013.01); *A61K 47/12* (2013.01); *A61K 47/14* (2013.01); *A61K 47/18* (2013.01); *A61K 47/26* (2013.01); *A61K 47/32* (2013.01); *A61K 47/44* (2013.01)

(58) Field of Classification Search
CPC combination set(s) only.
See application file for complete search history.

(56) References Cited

FOREIGN PATENT DOCUMENTS

| | | | | |
|---|---|---|---|---|
| CN | 1166963 A | | 12/1997 | |
| CN | 1511541 A | | 7/2004 | |
| CN | 1679622 A | | 10/2005 | |
| CN | 101934016 A | * | 1/2011 | |
| CN | 102421446 A | * | 4/2012 | ............ A61K 33/04 |
| CN | 102421446 A | | 4/2012 | |
| CN | 102940284 A | | 7/2013 | |
| CN | 105434465 A | | 3/2016 | |

OTHER PUBLICATIONS

Al-Ali, et al.; Clinical Evaluation of Zinc Therapy in Rheumatoid Arthritis; 2007; Medical Journal of Basrah University; 25(2):1-4 (Year: 2007).*
Gupta et al.; "Zinc Therapy in Dermatology: A Review"; 2014; Dermatology Research and Practice (2014): 1-11; http://dx.doi.org/10.1155/2014/709152 (Year: 2014).*
Bou et al. ("Effect of Dietary Fat Sources and Zinc and Selenium Supplements on the Composition and Consumer Acceptability of Chicken Meat"; 2005; Poultry Science; 84:1129-1140 (Year: 2005).*
Chinese First Office Action dated Dec. 14, 2017, Application No. 201510926291.1.
PCT International Preliminary Report on Patentability dated Jun. 28, 2018, Application No. PCT/CN2016/099076.
PCT International Search Report dated Dec. 12, 2016, Application No. PCT/CN2016/099076.
PCT Written Opinion dated Dec. 12, 2016, Application No. PCT/CN2016/099076.
Wang, Zixu et al., "Effect of Interaction Between Zinc and Selenium on Immune Function of Animals", Progress in Veterinary Medicine, vol. 24, No. 4, Aug. 31, 2003, pp. 33-35.
Zhu, Songjie, "Oral Administration of Zinc Sulphate for Treating Rehumatoid Arthritis", Reference Material of Foreign Medical Sciences (Internal Medicine Fascicle), No. 8, Dec. 31, 1977, p. 358.

* cited by examiner

*Primary Examiner* — Timothy P Thomas
(74) *Attorney, Agent, or Firm* — The Dobrusin Law Firm, PC

(57) ABSTRACT

This invention discloses a pharmaceutical formula for arthritis treatment and/or prevention. The formula contains the following raw materials: a selenium-containing inorganic compound and a zinc-containing inorganic compound. The pharmaceutical formula described herein could be manufactured for topic application and provide a faster and safer treatment for various inflammatory joint pains. Pharmacodynamics results show that the invented pharmaceutical formula can significantly reduce the level of inflammatory cytokines in the joint synovial fluid in arthritis rabbit model, and the formulated ointment can achieve better efficacy compared with Voltaren™ (diclofenac) ointment; therefore the proposed formula has promising clinical application.

3 Claims, No Drawings

PHARMACEUTICAL FORMULA FOR THE TREATMENT AND/OR PREVENTION OF ARTHRITIS AND ITS MANUFACTURE

TECHNICAL FIELD

This invention describes formulation of a pharmaceutical drug for the treatment of arthritis and its preparation method therefore it is in the field of medicine.

BACKGROUND

Arthritis refers to inflammatory diseases occurring in the joints and surrounding tissues which contains dozens of subtypes. One of the most common arthritis, osteoarthritis is a degenerative joint disease. Other arthritis include rheumatoid arthritis, gouty arthritis et al. The etiology of these diseases is not completely understood; and clinical manifestations include red and swollen joints; elevated temperature, pain, joint dysfunction and deformity. The commonly used anti-inflammatory drugs include non-steroidal anti-inflammatory drugs, such Ibuprofen, aspirin, diclofenac et al. The Voltaren™ ointment containing diclofenac as the main active ingredient is the mostly widely used drug for arthritis treatment. However, side effect such as stimulation of the gastrointestinal mucosa greatly limits the clinical application of these drugs. There is a great need of new treatment alternatives with effective efficacy and minimal side effects for arthritis.

Both selenium and zinc are essential micronutrient for human and animals. They play critical roles in normal physiology. In some areas in China, selenium deficiency leads to endemic disease. For example, the lack of selenium in the diet of population living in Qinghai-Tibet Plateau, high prevalence of Kashin-Beck disease is observed, which is manifested by arthritis. Sodium selenite is a well adopted selenium-containing inorganic compound diet supplement for people with selenium-deficiency. There are a number of pharmaceutical companies in China and outside of China manufacture sodium selenite tablets for the treatment and prevention of endemic diseases include Keshan disease and Kashin-Beck disease; The patent CN 1511541A, CN 1679622A also disclose and patent the use of tablets, granules, capsules and oral preparations containing sodium selenite as an active ingredient as drugs to treat osteoarthritis and rheumatoid arthritis. In addition, inorganic zinc compound, such as zinc chloride, is clinical used to treat acute or subacute dermatitis, eczema, prickly heat and mild, small area of skin ulcers as topical ointment. However, there has been no report using inorganic selenium and zinc synergistically in the treatment of arthritis.

DETAILED DESCRIPTION

This invention is to provide a novel pharmaceutical formula for the prevention and treatment of arthritis. This formula have advantages over conventional drugs with problems including poorer treatment effects, requirement for oral administration, and side effects caused by stimuli of gastrointestinal mucosa.

This invention provides a pharmaceutical formula for the treatment of arthritis which is comprised of following chemical compounds in the manufacture: an inorganic selenium compound and an inorganic zinc compound Furthermore, it is manufactured from the following compounds: inorganic zinc, 1 to 5 parts (by weight ratio); inorganic selenium compound, 1 to 5 parts (by weight ratio).

A preferable formula is manufactured by mixing selenium and zinc compounds with the following weight ratio: inorganic zinc (3 parts) of inorganic selenium (3 parts).

Furthermore, the inorganic zinc compound is selected from zinc sulfate, zinc chloride or zinc acetate. The inorganic selenium compound is sodium selenite. Wherein formulation is prepared from each of the ingredients with designated weight ratio, and with pharmaceutically acceptable excipient or adjuvant ingredients.

Furthermore, the formulated product is for topical use. The formulated product is preferably in the form of gels, creams, ointments or patches.

This invention provides a manufacture method of a pharmaceutical formula which containing the following steps: Weigh each ingredients of proposed formula with a designated ratio; add pharmaceutically acceptable excipients or adjuvant. The final product is derived.

This invention also provides a pharmaceutical formula applied as a treatment and/or preventative drug for arthritis.

Furthermore, the formulated drug is targeted for the treatment and/or prevention of osteoarthritis, rheumatoid arthritis, gouty arthritis, reactive arthritis, infectious arthritis, traumatic arthritis, carpal tunnel syndrome and bursitis.

Preferably, the formulated drug targets for the treatment and/or prevention of osteoarthritis.

This invention provides a pharmaceutical formula for the prevention and treatment of arthritis. It can be formulated for topical use, providing a quicker and safer treatment for various joint pain. Selenium has therapeutic effect for arthritis; however, cellular permeation of inorganic selenium into inflammatory cells is limited. This invention thus solves this problem through adjuvant zinc co-administration to stimulate selenium cellular uptake and permeation. The experiment results showed that the formula proposed in this invention can significantly reduce the levels of inflammatory cytokines in the synovial fluid using arthritis rabbit model, and the formulated ointment can achieve better treatment efficacy than Voltaren™ ointment. Therefore it has great potential in future clinical application.

Apparently, following this invention, additional modifications, substitution, and alterations could be stemmed from the fundamental technique discussed in this invention, in accordance with the well adopted technical knowledge and commonly accepted principles in the field. All technique based on or stemmed from the fundamental principles are within the scope of this invention.

The described invention is described in more details with case studies and examples, as listed below. They are examples when invention is formulated and manufactured. However, it does not include all cases and the scope of this invention is not limited to these examples.

All raw materials and equipment involved in the following examples based on this invention are commercial products which can be purchased from certified vendors.

Example 1

Formulation and manufacture of gel product following principles proposed in the invention.

Formula: zinc sulfate 0.10 g, sodium selenite 0.10 g, carbomer 940 10 g, glycerol 75 g, polysorbate 80 2 g, triethanolamine 13.5 g, adding distilled water to a final weight of 1000 g.

Process: Mix carbomer 940, polysorbate 80 and 300 g of distilled water; Dissolve triethanolamine in 100 g distilled water and add it to the above mixture; add glycerol and mix well to obtain the matrix. Active ingredients zinc sulfate and sodium selenite are completely dissolved in 250 g of distilled water. The solution is added to the matrix; and add water to a final weight of 1000 g. The gel is mixed completely and bubbles are removed. The gel product is obtained and named ZJ-1.

Example 2

Formulation and manufacture of gel product following principles proposed in the invention.

Formula: zinc sulfate 0.5 g, sodium selenite 0.1 g, carbomer 940 10 g, glycerol 75 g, polysorbate 80 2 g, triethanolamine 13.5 g, adding distilled water to a final weight of 1000 g.

Process: Mix carbomer 940, polysorbate 80 and 300 g of distilled water; Dissolve triethanolamine in 100 g distilled water and add to the above mixture; add glycerol and mix well to obtain the matrix. Active ingredients zinc sulfate and sodium selenite are completely dissolved in 250 g of distilled water. The solution is added to the matrix; and add water to a final weight of 1000 g. The gel is mixed completely and bubbles are removed. The gel product is obtained and named ZJ-2.

Example 3

Formulation and manufacture of gel product following principles proposed in the invention.

Formula: 0.5 g of zinc sulfate, 0.5 g of sodium selenite, 100 g of white petrolatum, 100 g of octadecanol, 50 g of liquid paraffin, 60 g of glyceryl monostearate, 10 g of OP emulsifier (alkylphenol ethoxylate) 20 g Peregal O, 50 g of glycerol, and 20 g of lauricotone.

Process: Mix white petrolatum, octadecanol, glyceryl monostearate, liquid paraffin, Peregal O and heated to 80 degrees till completely dissolved. The oil phase is separated. Mix zinc chloride, lauric acid, sodium selenite, glycerol, OP emulsifier with 300 mL water, and add oil phase, emulsify for 20 minutes, finished by adding water to 1000 ml, the cream ZJ-3 is then accomplished.

Example 4

Formulation and manufacture of gel product following principles proposed in the invention.

Formula: zinc sulfate 0.1 g, sodium selenite 0.5 g, stearic acid 120 g, glyceryl monostearate 30 g, liquid paraffin 50 g, petrolatum 12 g, lanolin 40 g, triethanolamine 3 g, adding distilled water to final weight 1000 g.

Process: Melt and mix stearic acid, glyceryl monostearate, liquid paraffin, petrolatum, lanolin; In parallel, zinc sulfate and sodium selenite, triethanolamine, Nepaline ethyl ester is heated melted in distilled water and mix well. This cream is poured into stearic acid mixture slowly, mix well till completely emulsified, ointment ZJ-4 is obtained.

Example 5

Formulation and manufacture of patch product following principles proposed in the invention.

Formula: 0.3 g of zinc sulfate, 0.3 g of sodium selenite, 60 g of gelatin, 100 g of cellulose sodium, 30 g of sodium polyacrylate, 120 g of kaolin, 80 g of PEG 400 (polyethylene glycol 400), 100 g of carbomer, 20 g of sorbitol, 200 g, water 290 g.

Process: All materials are well mixed, and applied on non-woven cloth with a back layer and an anti-stick layer to obtain the patch named as ZJ-5.

Example 6

Formulation and manufacture of gel product following principles proposed in the invention.

Formula: zinc sulfate 0.5 g, sodium selenite 0.10 g, carbomer 940 10 g, glycerol 75 g, polysorbate 80 2 g, triethanolamine 13.5 g, adding distilled water to a final weight of 1000 g.

Process: Mix carbomer 940, polysorbate 80 and 300 g of distilled water; Dissolve triethanolamine in 100 g distilled water and add to the above mixture; add glycerol and mix well to obtain the matrix. Active ingredients zinc sulfate and sodium selenite are completely dissolved in 250 g of distilled water. The solution is added to the matrix; and add water to a final weight of 1000 g. The gel is mixed completely and bubbles are removed. The gel product is obtained and named ZJ-6.

Example 7

Formulation and manufacture of gel product following principles proposed in the invention.

Formula: zinc sulfate 0.3 g, sodium selenite 0.3 g, carbomer 940 10 g, glycerol 75 g, polysorbate 80 2 g, triethanolamine 13.5 g, adding distilled water to a final weight of 1000 g.

Process: Mix carbomer 940, polysorbate 80 and 300 g of distilled water; Dissolve triethanolamine in 100 g distilled water and add to the above mixture; add glycerol and mix well to obtain the matrix. Active reagents zinc sulfate and sodium selenite are completely dissolved in 250 g of distilled water. The solution is added to the matrix; and add water to a final weight of 1000 g. The gel is mixed completely and bubbles are removed. The gel product is obtained and named ZJ-7.

Example 8

Formulation and manufacture of gel product following principles proposed in the invention.

Formula: zinc chloride 0.1 g, sodium selenite 0.5 g, white petrolatum 100 g, octadecanol 100 g, liquid paraffin 50 g, glyceryl monostearate 60 g, OP emulsifier 10 g, Peregal 0 20 g, glycerin 50 g, laurel azaphorone 20 g.

Process: Mix white petrolatum, octadecyl alcohol, glyceryl monostearate, liquid paraffin, peregal 0 and heat to 80 degrees till completely melted. The oil phase is separated. Mix zinc chloride, lauric acid, sodium selenite, glycerol, OP emulsifier with water 300 ml, and add oil phase, emulsify for 20 minutes, finished by adding water to 1000 ml, the cream ZJ-8 is obtained.

The beneficial effects of formula proposed in this invention are demonstrated by drug efficacy test using appropriate controls and above described formulated drugs.

Control Example 1

Formulation and Manufacture of Zinc Gel

Formula: zinc sulfate 0.5 g, carbomer 940 10 g, glycerol 75 g, polysorbate 80 2 g, triethanolamine 13.5 g, distilled water to 1000 g.

Process: Mix carbomer 940, polysorbate 80 and 300 g of distilled water; dissolve triethanolamine in 100 g distilled water and add to the above mixture; add glycerol and mix well to obtain the matrix. Zinc sulfate is completely dissolved in 250 g of distilled water. The solution is added to the matrix; and water is added to a final weight of 1000 g. The gel is mixed completely and bubbles are removed. The control gel product is obtained and named ZN.

Control Example 2

Formulation and Manufacture of Selenium Gel

Formula: sodium selenite 0.5 g, carbomer 940 10 g, glycerol 75 g, polysorbate 80 2 g, triethanolamine 13.5 g, distilled water to 1000 g.

Process: Mix carbomer 940, polysorbate 80 and 300 g of distilled water; dissolve triethanolamine in 100 g distilled water and add to the above mixture; add glycerol and mix well to obtain the matrix. Sodium selenite are completely dissolved in 250 g of distilled water. The solution is added to the matrix; and water is added to a final weight of 1000 g. The gel is mixed completely and bubbles are removed. The control gel product is obtained and named SE.

Animal Experiment to Determine Efficacy

Generally adopted biomarkers for inflammation include cytokines and chemokines such as TNF-α (tumor necrosis factor-alpha), NF-kB (transcription factor protein family), or IL (interleukin).

Objective

To investigate the effects of the proposed formula in this invention on the levels of cytokines (TNF-α and IL-1β) in rabbits with knee osteoarthritis (OA).

Materials and Methods

Experimental animals: A total number of 130 of healthy New Zealand white rabbits with equal numbers of males and females are used. These animals have weight range of 2.5-3 Kg and are supplied by Chengdu Dashuo Experimental Animal Ltd. The animal are fed with regular chew. They are raised at room temperature 15-25° C. with regular light cycle and fine air circulation in cages with free access to food and water.

Chemicals

Drugs for animal treatment are prepared as described in examples (1 to 8, and SE and ZN). Positive control Drug is Voltaren™ Ointment.

Major reagents and instruments: TNF-α radioimmunoassay kit; IL-1β radioimmunoassay kit; Electronic balance (ME2355 type, SARTORIUS company), adjustable pipettes with different ranges and matching tips, low-speed centrifuge, mixers, rabbit fixing stage, refrigerators and freezers.

Experimental Protocol

The total 130 animals are divided into 13 groups: untreated non-diseased; untreated diseased model group, ZN group (treated by Zinc only), SE group (treated by Selenite only), treatment group, and group 1-8. Each group contains 10 animals and their weight are recorded.

Surgical Procedure to Create OA Diseased Animal Model

Except for non-diseased control group, all animals are given surgery to create OA diseased animal model using Vandman method. Left knee joint of experimental animals are extended and the leg from 3 cm above ankle to 1.5 cm below groin are fixed with dorsiflexion 30-40°. The fixation last for 6 weeks. After 6 weeks of immobilization, one from each group of animals is sacrificed and the articular cartilage is isolated for pathological examination to show the OA progresses. Fixation is removed and joint skin is shaved for treatment.

Treatment

Following the OA animal model established, the control group will be treated by coating with Voltaren™ ointment with a thickness of 2 mm applying uniformly on joint surface at 2 times a day. The treatment groups are treated with the patch, ointment or gel as described in Examples (1 to 8) with a thickness of approximately 2 mm at a frequency of twice daily. ZN and SE group are treated with gels prepared as described, both are applied with a thickness of 2 mm twice daily. Untreated group OA diseased animals and non-diseased control animals are applied Vaseline cream with a thickness of 2 mm twice daily.

Joint Synovial Fluid Extraction

After treatment for 8 weeks, the rabbits are sacrificed by air injection in ear vein with a volume of 30 ml. The rabbits are fixed on the anatomy shelf. Knee skin is exposed and disinfected. A needle is inserted inward 0.5 cm above the patellar ligament, and 1.5 ml of distilled water is injected into the joint cavity and mixed with synovial fluid. Approximately 2 ml synovial fluid mixture is extracted. After centrifuge at 4000 r/min for 10 min, 0.3 m L supernatant is transferred to test tube and stored at −20° C. freezer to be assayed. Levels of TNF-α and IL-1β are quantified in these synovial fluid samples following instruction provided by providers included in commercial kits.

Statistics

The experimental data are presented as mean±standard deviation (x±s), and t or t 'test is used to compare between pairs. The test level is α=0.05; and results are analyzed by SPSS 17.0 software.

Experiment Results

TABLE 1

Effects of the pharmaceutical formula of this invention on the levels of cytokines TNF-α and IL-1β in synovial fluid of rabbits with knee osteoarthritis

| Groups | Numbers | TNF-α (ng/mL) | IL-1β (ng/mL) |
| --- | --- | --- | --- |
| Non-diseased animal | 10 | 1.75 ± 0.28** | 0.29 ± 0.05** |
| Diseased (OA model) | 10 | 2.72 ± 0.21 | 0.52 ± 0.06 |
| Untreated Control | 10 | 2.27 ± 0.26** | 0.32 ± 0.08** |
| Zn alone | 10 | 2.70 ± 0.18 | 0.50 ± 0.05 |
| Se alone | 10 | 2.59 ± 0.17 | 0.48 ± 0.07 |
| ZJ-1 | 10 | 2.24 ± 0.22** | 0.36 ± 0.07** |
| ZJ-2 | 10 | 2.30 ± 0.29** | 0.34 ± 0.05** |
| ZJ-3 | 10 | 2.30 ± 0.13** | 0.34 ± 0.06** |
| ZJ-4 | 10 | 2.25 ± 0.26** | 0.35 ± 0.06** |
| ZJ-5 | 10 | 2.13 ± 0.22** | 0.33 ± 0.05** |
| ZJ-6 | 10 | 2.45 ± 0.31* | 0.34 ± 0.09** |
| ZJ-7 | 10 | 2.35 ± 0.20** | 0.40 ± 0.13* |
| ZJ-8 | 10 | 2.32 ± 0.24** | 0.36 ± 0.13** |

The levels of TNF-α and IL-1β in the synovial fluid of the non-diseased controls are significantly lower than those in the OA diseased model group (P<0.01), which indicate that the inflammatory cytokines in the left knee joint are increased in OA animals.

The levels of TNF-α and IL-1β in the treatment group are significantly lower than those in the OA diseased group (P<0.01), which demonstrated that the pharmaceutical formula of the invention can significantly reduce the levels of inflammatory cytokines in synovial fluid with arthritis.

When selenium or zinc treatment is performed alone, there is no significant difference in the levels of TNF-α and IL-1β in the joint synovial fluid between OA diseased model group and treatment group, showing the poor anti-inflammatory effect by selenium or zinc alone. When applied synergistically with an appropriate ratio of inorganic selenium and zinc compounds proposed in this invention, significant anti-inflammatory effects are observed.

These experimental results demonstrated that the pharmaceutical formula in this invention has a significant therapeutic effect on arthritis. The ZJ-5 formula can achieve better efficacy than Voltaren™ ointment

The invention claimed is:

1. A pharmaceutical formula comprising a selenium-containing inorganic compound and a zinc-containing inorganic compound formed in a gel matrix or cream for topical application to skin, including:
   from 0.05 g to 0.8 g zinc sulfate;
   from 0.05 g to 0.8 g sodium selenite;
   from 5 g to 15 g carbomer 940;
   from 50 g to 90 g glycerol;
   from 0.5 g to 8 g polysorbate 80; and
   from 5 g to 25 g triethanolamine, distilled water so that the final weight of the pharmaceutical formula is 1000 g.

2. A pharmaceutical formula comprising a selenium-containing inorganic compound and a zinc-containing inorganic compound formed in a gel matrix or cream for topical application to skin, including from 0.05 g to 0.8 g zinc sulfate and from 0.05 g to 0.8 g sodium selenite per 1000 g of the formula.

3. A pharmaceutical formula comprising a selenium-containing inorganic compound and a zinc-containing inorganic compound formed in a gel matrix or cream for topical application to skin, including from about 0.1 g to 0.5 g zinc sulfate and from 0.1 g to 0.5 g sodium selenite per 1000 g of the formula.

* * * * *

UNITED STATES PATENT AND TRADEMARK OFFICE
CERTIFICATE OF CORRECTION

PATENT NO. : 10,485,826 B2
APPLICATION NO. : 15/544641
DATED : November 26, 2019
INVENTOR(S) : Zijuan Liu Page 1 of 1

It is certified that error appears in the above-identified patent and that said Letters Patent is hereby corrected as shown below:

On the Title Page

Column 1, Item (71) Applicant:
Delete "Jun Mi, Sichuan (CN)"
And insert --Zoesen LLC, Rochester Hills, MI (US)--

Signed and Sealed this
Seventh Day of January, 2020

Andrei Iancu
*Director of the United States Patent and Trademark Office*